(12) United States Patent
Reddy et al.

(10) Patent No.: US 8,362,279 B2
(45) Date of Patent: Jan. 29, 2013

(54) PROCESS FOR PURE DULOXETINE HYDROCHLORIDE

(75) Inventors: Manne Satyanarayana Reddy, Hyderabad (IN); Muppa Kishore Kumar, Hyderabad (IN); Srinivasan Thirumalai Rajan, Hyderabad (IN); Durgadas Shyla Prasad, Hyderabad (IN)

(73) Assignee: MSN Laboratories Limited, Andhra Pradesh, Hyderabad (IN)

( * ) Notice: Subject to any disclaimer, the term of this patent is extended or adjusted under 35 U.S.C. 154(b) by 1183 days.

(21) Appl. No.: 12/087,350

(22) PCT Filed: Jan. 4, 2007

(86) PCT No.: PCT/IN2007/000003
§ 371 (c)(1),
(2), (4) Date: Aug. 20, 2008

(87) PCT Pub. No.: WO2007/077580
PCT Pub. Date: Jul. 12, 2007

(65) Prior Publication Data
US 2009/0012315 A1    Jan. 8, 2009

(30) Foreign Application Priority Data

Jan. 6, 2006  (IN) ............................ 30/CHE/2006
Dec. 11, 2006 (IN) ......................... 2296/CHE/2006

(51) Int. Cl.
*C07D 333/16*    (2006.01)
(52) U.S. Cl. ............................................. 549/75
(58) Field of Classification Search ................ None
See application file for complete search history.

(56) References Cited

U.S. PATENT DOCUMENTS 5,023,269 A    6/1991  Robertson et al.
5,362,886 A   11/1994  Berglund
5,491,243 A    2/1996  Berglund
2005/0197503 A1  9/2005  Schiffers et al.
2008/0015363 A1*  1/2008  Ini et al. .................... 549/75

FOREIGN PATENT DOCUMENTS

| EP | 0273658 B1 | 7/1988 |
| EP | 0457559 A2 | 11/1991 |
| EP | 0650965 B1 | 5/1995 |
| WO | WO 2006099433 A1 | 9/2006 |

OTHER PUBLICATIONS

Gao et al. (Chinese Journal of New Drugs, vol. 14, No. 1, pp. 74-76).*
English translation of Gao et al. (Chinese Journal of New Drugs, vol. 14, No. 1, pp. 74-76). Translated by Schreiber Translations, Inc in Mar. 2012.*
Gao et al. (Chinese Journal of New Drugs, vol. 14, No. 1, pp. 74-76, 2005).*
Luo, G., et al. "An Improved Synthesis Method of Antidepressant Drug Duloxetine Hydrochloride.Yaouxue J." (2006), 30(4), 181-184, Columbus Ohio, USA: Chemical Abstracts vol. 146, Jun. 21, 2006, the abstract No. 592369.
PCT Written Opinion of the International Searching Authority from PCT/IN2007/000003, Dated: Mar. 3, 2008.

* cited by examiner

Primary Examiner — Joseph K. McKane
Assistant Examiner — Alicia L Otton
(74) Attorney, Agent, or Firm — Hamilton, Brook, Smith & Reynolds, P.C.

(57) ABSTRACT

A process for the preparation of pure Duloxetine hydrochloride comprises the steps of: a) reacting 1-(thiophen-2-yl) ethanone with dimethylamine hydrochloride, b) purifying the component in a solvent, c) reducing the component with an alkali metal borohydride, d) resolving the compound with a chiral acid, and treating the obtained compound with weak inorganic base, e) reacting the compound to give Duloxetine oxalate salt and f) converting the Duloxetine salt into its hydrochloride salt. Further the purifications of the obtained compound and of two intermediate products are described.

16 Claims, 2 Drawing Sheets

PROCESS FOR PURE DULOXETINE HYDROCHLORIDE

RELATED APPLICATIONS

This application is the U.S. National Stage of International Application No. PCT/IN2007/000003, filed Jan. 4, 2007, published in English, and claims priority under 35 U.S.C. §119 or 365 to Indian Application No. 2296/CHE/2006 filed Dec. 11, 2006 and Indian Application No. 30/CHE/2006, filed Jan. 6, 2006.

FIELD OF INVENTION

The present invention relates to an improved process for the preparation of pure Duloxetine hydrochloride substantially free from impurities. Duloxetine hydrochloride is chemically known as (S)-(+)-N-methyl-3-(1-naphthalenyloxy)-3-(2-thienyl) propanamine hydrochloride compound of formula-1 represented as follows Formula-1

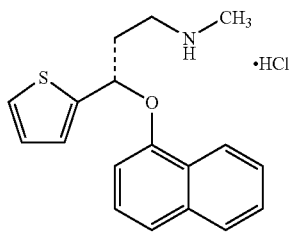

Duloxetine and related class of compounds like fluoxetine, tomoxetine etc., are important for treating psychiatric disorders. Fluoxetine is selective inhibitor of serotonin in serotonergic neurons; tomoxetine and nisoxetine are selective inhibitors of norepinephrine in noradrenergic neurons while duloxetine is a dual inhibitor of serotonin and norepinephrine reuptake and thus have a better pharmacological profile as an antidepressant drug.

Serotonin and norepinephrine neuro transmitters are intimately involved in a number of physiological and behavioral processes, suggesting that duloxetine (ability to produce robust increase of extra cellular serotonin and norepinephrine levels) is not only a highly efficient antidepressant agent for treating psychiatric disorders but also can be used for treating other symptoms like alcoholism, urinary incontinence, fatigue, stroke, intestinal cystitis, obsessive compulsive disorder, panic disorder, hyperactivity disorder, sleep disorder, sexual dysfunction etc. It is commercially available as CYMBALTA®.

BACKGROUND OF THE INVENTION

Synthesis of duloxetine is described in detail in EP-A-273 658, EP-A-457 559 and EP-A-650965, starting from 2-acetylthiophene, an aminomethylation with dimethylamine and formaldehyde (Mannich reaction) is carried out in step-A. The 3-dimethylamino-1-(2-thienyl)-1-propanone formed is reduced to the corresponding alcohol 1-hydroxy-1-(2-thenyl)-3-dimethylaminopropane by means of complex hydrides in step B. The alcohol is then converted in step C with an alkali metal hydride and 1-fluoro-naphthalene, optionally in the presence of a potassium compound (cf. EP-A-650 965), to the naphthyl derivative, N,N-dimethyl-3-(1-naphthyloxy)-3-(2-thienyl) propylamine. In the final step D, the amino group is then demethylated by reaction with a chloroformic acid ester, preferably phenyl chloroformate or trichloroethyl chloroformate, optionally in the presence of a mixture of zinc and formic acid (EP-A-457 559), followed by alkaline hydrolysis of the carbamate to give N-methyl-3-(1-naphthyloxy)-3-(2-thienyl) propylamine.

The EP patent 457559 described the process for the preparation of duloxetine comprises of using alkali metal hydride like sodium hydride, which is commercially not recommendable.

The U.S. Pat. No. 5,362,886 described the process for the preparation of (+)Duloxetine hydrochloride by isolating the (S)-(+)-N,N-dimethyl-3-(1-naphthalenyloxy)-3-(2-thienyl) propanamine phosphoric acid salt and preparation of hydrochloride salt using aqueous hydrochloric acid and ethyl acetate as a solvent.

The U.S. Pat. No. 5,023,269 claims Duloxetine and its pharmaceutically acceptable salts and method of treating anxiety and obesity. The patent also discloses the processes for the preparation of Duloxetine and its pharmaceutically acceptable salts, however the patent not disclosed the process for the preparation of hydrochloride salt.

The EP patent 0650965 B1 discloses the process for the preparation of (S)-(+)-N,N-dimethyl-3-(1-naphthalenyloxy)-3-(2-thienyl)propanamine an intermediate of Duloxetine which was isolated as a phosphoric acid salt and disclosed the process for the preparation of Duloxetine hydrochloride using aqueous hydrochloric acid and ethyl acetate as a solvent.

The U.S. Pat. No. 5,491,243 and U.S. Pat. No. 5,362,886 discloses the stereospecific process for the synthesis of (S)-(+)-N,N-dimethyl-3-(1-naphthalenyloxy)-3-(2-thienyl)propanamine and claimed the same. In both the patents the above said compound isolated as a phosphoric acid salt.

Like any chemical compound, duloxetine hydrochloride can contain extraneous compounds or impurities that can come from many sources. They can be unreacted starting materials, by-products of the reaction, products of side reactions, or degradation products. Impurities in duloxetine hydrochloride or any active pharmaceutical ingredient are undesirable, and in extreme cases, might even be harmful to a patient being treating with a dosage form of the active pharmaceutical ingredient in which a sufficient amount of impurities is present. Furthermore, the undesired enantiomeric impurities reduce the sufficient level of active pharmaceutical ingredient present in the pharmaceutical composition.

It is also known in the art that impurities in an active pharmaceutical ingredient may arise from degradation of the active pharmaceutical ingredient itself, which is related to the stability of the pure active pharmaceutical ingredient during storage, and the manufacturing process, including chemical synthesis. Process impurities which include unreacted starting materials, chemical derivatives of impurities contained in the starting materials, synthetic by-products, and degradation products.

In addition to stability, which is factor in the shelf life of the active pharmaceutical ingredient, the purity of the active pharmaceutical ingredient in the commercial manufacturing process is clearly a necessary condition for commercialization. Impurities introduced during commercial manufacturing processes must be limited to very small amounts, and are preferably substantially absent. For example, the ICH Q7A guidance for active pharmaceutical ingredient manufacturers requires that process impurities be maintained below set limits by specifying the quality raw materials, controlling process parameters, such as temperature, pressure, time and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during the preparation process, it should be analyzed for the purity by HPLC or TLC analysis to determine if it is desirable for continue the process or need to purified further to continue the process especially for use in a pharmaceutical product. The active pharmaceutical ingredient need not be absolutely pure, as absolute purity is a theoretical ideal that is typically unattainable. Rather the purity standards are set with the intension of ensuring that an active pharmaceutical ingredient is as free of impurities as possible, and thus, is as safe as possible for clinical use.

Duloxetine hydrochloride prepared as per the prior art process containing the isomer impurity (+)-N-methyl-3(1-naphtalenyloxy)-3-(3-thienyl) propanamine, referred to herein as "DU-I" (represented below) and other undesired isomer i.e., R-isomer of Duloxetine hydrochloride.

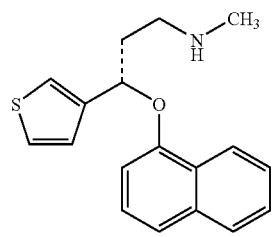

"DU-I"

The impurity "DU-I" is formed due to the carry over of isomer, i.e., 3-acetyl thiophene compound of formula 2I as an impurity present in 2-acetyl thiophene compound of formula 2. The formation of isomer "DU-I" during the preparation of duloxetine hydrochloride schematically represented in scheme-1, in which the Formula-4I, 5I, 6I and 8I represents the corresponding derivatives of isomer impurity formation in each stage.

Scheme-1:
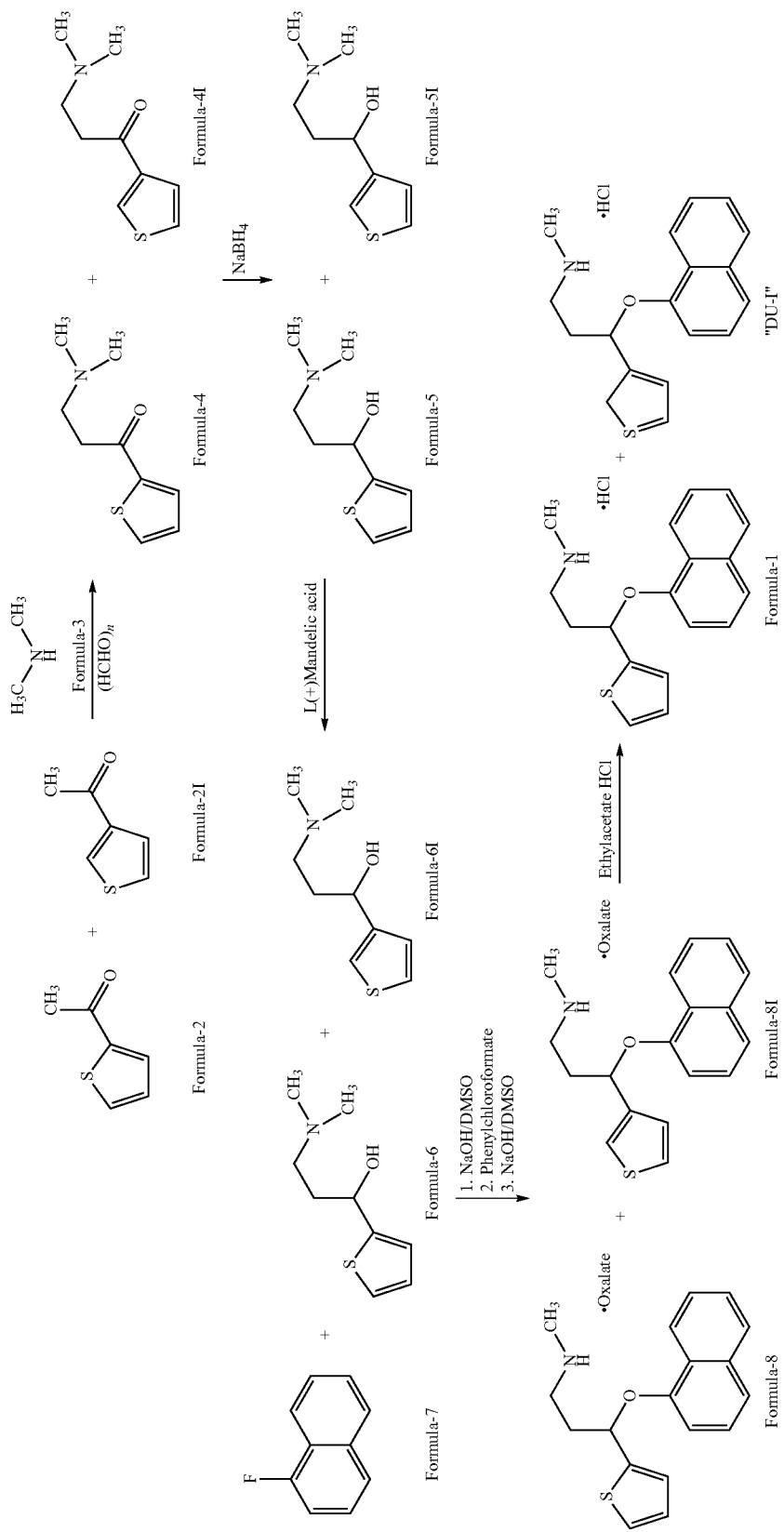

The international patent publication WO 2006/099433 disclosed the process for the purification of duloxetine hydrochloride to reduce the (+)-N-methyl-3-(1-napthalenyloxy)-3 (3-thineyl) propanamine isomer impurity i.e. "DU-I". The said patent disclosed the process for the purification of Duloxetine hydrochloride to reduce the level of said isomer content. Generally purification at the final stage of any compound leads to loss of material which increases cost of production which is not recommended for commercial scale-up.

We, the present inventors found the origin of isomer impurity ("DU-I") formation (represented in scheme-1) is due to the presence of 3-acetyl impurity in the starting material 2-acetyl compound of formula-2.

When we were working to eliminate the "DU-I" impurity in the origin itself, surprisingly found that the purity of Duloxetine hydrochloride has been increased by employing purification at first stage. The purification of compound of formula-4, then usage of this pure intermediate in the preparation of Duloxetine hydrochloride gives high pure Duloxetine hydrochloride which is free from the said isomer impurity. Purification of mandelate salt of (S)-3-(dimethylamino)-1-(thiophen-2-yl) propan-1-ol in a suitable solvent to eliminate the corresponding derivative of R-isomer in an early stage. By employing purification at the initial stages instead of final stage avoids the usage of high inputs of raw materials, which avoids increase in cost of production.

The main objective of the present invention is to provide an improved process for the preparation of high pure Duloxetine hydrochloride substantially free from impurities such as (+)-N-methyl-3-(1-napthalenyloxy)-3(3-thineyl) propanamine impurity ("DU-I") and undesired (R)-isomer of Duloxetine hydrochloride.

DISADVANTAGEOUS OF THE PRIOR ART PROCESSES

The EP patent 457559 uses alkali metal hydride like sodium hydride in the preparation of duloxetine, which is commercially not recommended.

Duloxetine hydrochloride prepared as per the prior art process having high level of impurities like DU-I and R-isomer of duloxetine hydrochloride.

The U.S. Pat. No. 5,362,886 describes the process for the preparation of (+) Duloxetine hydrochloride by isolating the (S)-(+)-N,N-dimethyl-3-(1-naphthalenyloxy)-3-(2 thienyl)propanamine as phosphoric acid salt leads to one more step and preparation of hydrochloride salt of Duloxetine using aqueous hydrochloric acid and ethyl acetate as a solvent leads to degradation of the obtained compound as shown below.

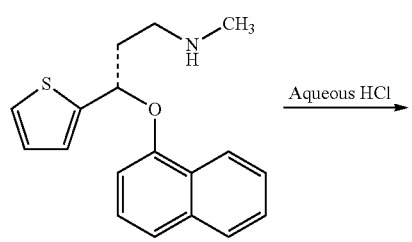

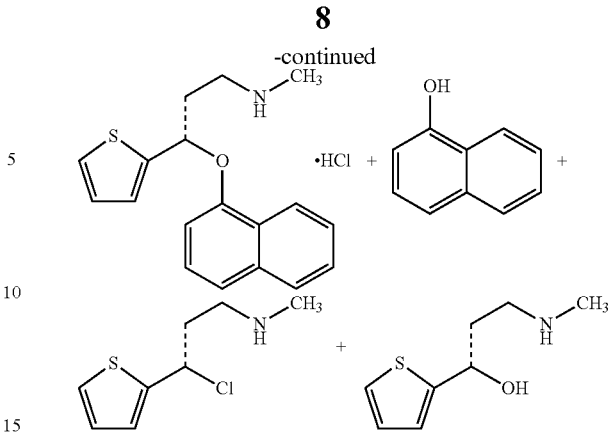

BRIEF DESCRIPTION OF THE INVENTION

Accordingly the present invention provides an improved process for the preparation of high pure Duloxetine hydrochloride substantially free from impurities such as (+)-N-methyl-3-(1-napthalenyloxy)-3(3-thineyl) propanamine impurity ("DU-I") and undesired (R)-isomer of Duloxetine hydrochloride. Duloxetine hydrochloride chemically known as (S)-(+)-N-methyl-3-(1-naphthalenyloxy)-3-(2-thienyl)-propanamine hydrochloride compound of formula-1 represented as below

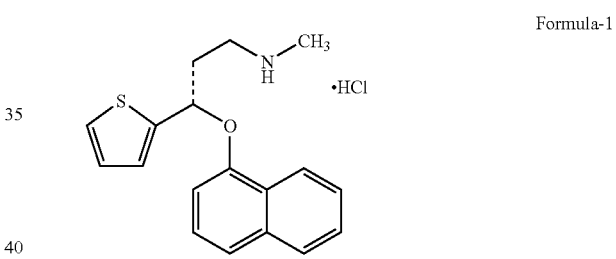

Formula-1

The present invention comprises of the following steps
a) Reacting 1-(thiophen-2-yl)ethanone compound of formula-2 with dimethylamine hydrochloride compound of formula-3 in presence of paraformaldehyde in a suitable solvent gives the compound of formula-4,
b) Purifying the compound of formula-4 in a suitable solvents and/or mixtures thereof to give the pure compound of formula-4,
c) Reducing the compound of formula-4 with an alkali metal borohydrides in a suitable solvent gives the compound of formula-5,
d) Resolving the compound of formula-5 with chiral acid in a suitable solvent followed by purifying the corresponding salt in a suitable solvent, further treating the obtained compound with weak inorganic base in a suitable chloro solvents or ester solvents gives the compound of formula-6,
e) Reacting the compound of formula-6 with the compound of formula-7 in presence of an alkali base and in a suitable polar aprotic solvent, which in situ demethylation followed by treating with oxalic acid gives Duloxetine Oxalate salt compound of formula-8,
f) Converting the Duloxetine oxalate salt compound of formula-8 into its hydrochloride salt compound of formula-1 using suitable alcoholic HCl or ester HCl in a suitable solvent like alcoholic solvents and/or ester solvents, g) Purifying the duloxetine hydrochloride compound of formula-1 using suitable alcohol and/or ester solvents and/or mixtures thereof.

ADVANTAGEOUS OF THE PRESENT INVENTION

Usage of ethyl acetate HCl for the preparation of Duloxetine hydrochloride instead of using aqueous hydrochloride for avoiding degradation of Molecule and to get the free flow material.

As per the present invention the isolation of (S)-(+)-N,N-dimethyl-3-(1-naphthalenyloxy)-3-(2-thienyl)propanamine as phosphoric acid salt is avoided.

Provided an improved process for the preparation of (S)-(+)-N-methyl-3-(1-naphthalenyloxy)-3-(2-thienyl) propanamine oxalate without isolating intermediate compounds (S)-(+)-N,N-dimethyl-3-(1-naphthalenyloxy)-3-(2-thienyl) propanamine and (S)-(+)-N-phenyloxy carbonyl-N-methyl-3-(1-naphthalenyloxy)-3-(2-thienyl) propanamine thereby reduces two steps in the synthesis of Duloxetine hydrochloride.

Provide an improved process for producing Duloxetine hydrochloride substantially free from R-isomer of Duloxetine hydrochloride.

Provided an improved process for Duloxetine hydrochloride substantially free from (+)-N-methyl-3-(1-napthalenyloxy)-3(3-thineyl) propanamine impurity (DU-I).

Removing of corresponding derivative of (+)-N-methyl-3-(1-napthalenyloxy)-3(3-thineyl) propanamine impurity by purification at the initial stage of the process avoids the usage of high inputs of raw materials which avoids increase in cost of production.

Removing R-isomer of Duloxetine hydrochloride by purification of Duloxetine hydrochloride in a suitable solvents.

Removing the corresponding derivative of R-isomer by purification of mandelate salt of (S)-3-(dimethylamino)-1-(thiophen-2-yl) propan-1-ol.

Present invention provides an improved process which is cost effective, eco-friendly and commercially scalable.

DETAILED DESCRIPTION OF THE INVENTION

Figure 1:
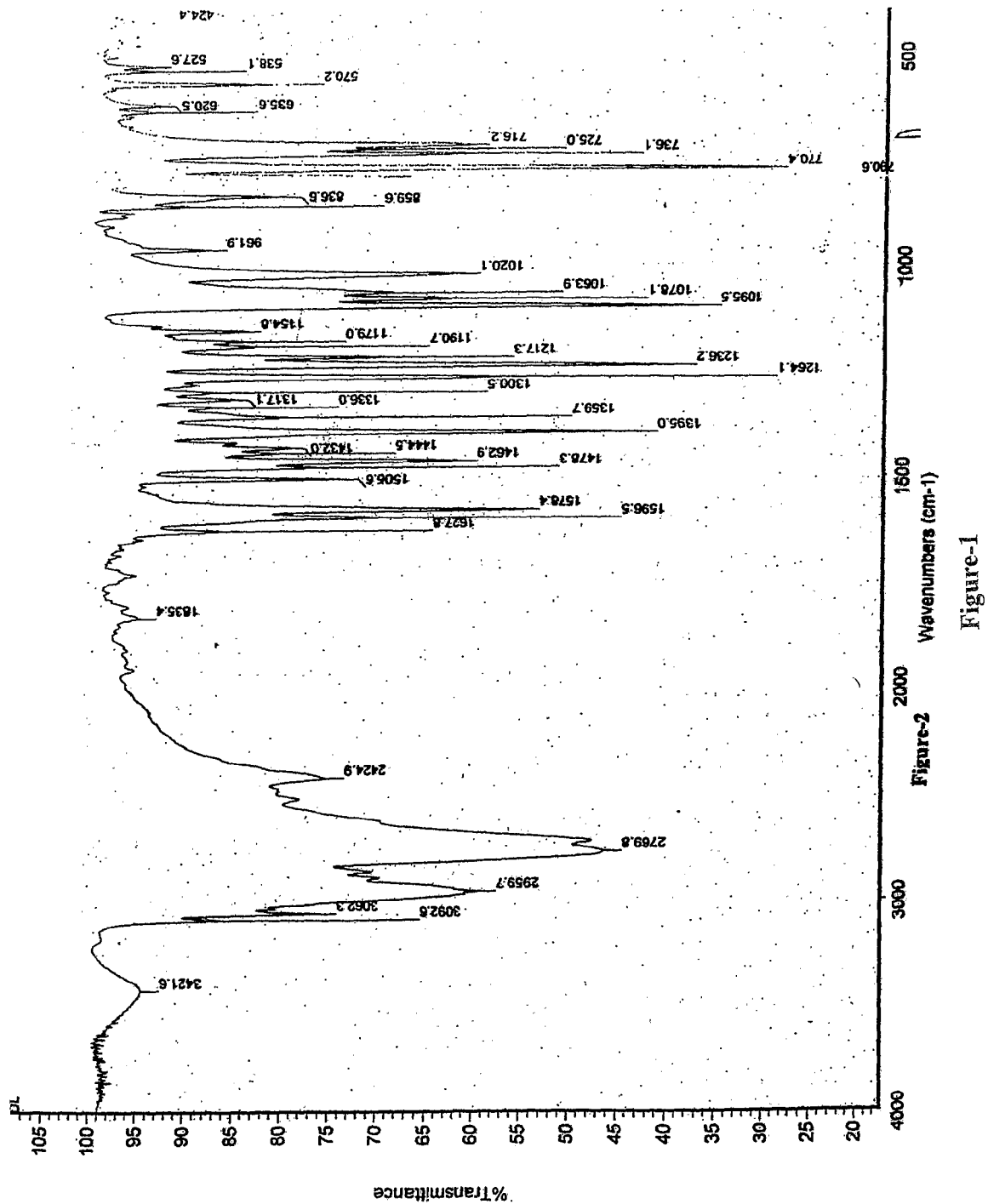
FIG. 1: Illustrates the DSC Thermo gram of Duloxetine hydrochloride.
Figure 2:
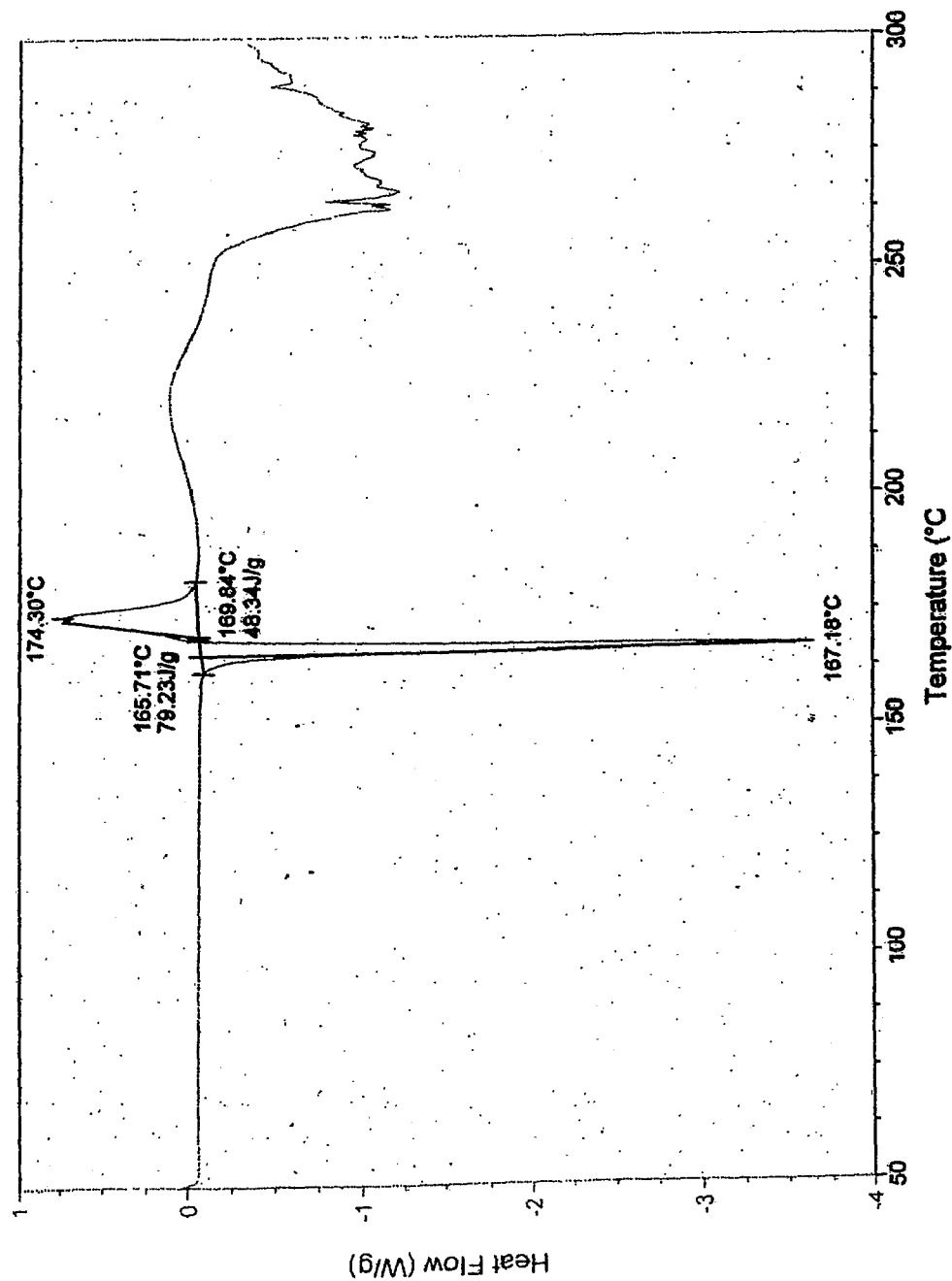
FIG. 2: Illustrates the IR spectrum of Duloxetine hydrochloride.

The present invention provides an improved process for the preparation of high pure Duloxetine hydrochloride substantially free from impurities such as (+)-N-methyl-3-(1-napthalenyloxy)-3(3-thineyl) propanamine impurity ("DU-I") and undesired (R)-isomer of Duloxetine hydrochloride. Duloxetine hydrochloride chemically known as (S)-(+)-N-methyl-3-(1-naphthalenyloxy)-3-(2-thienyl)-propanamine hydrochloride compound of formula-1 represented as below

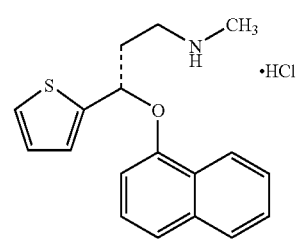

Formula-1

The present invention comprises of the following steps
a) Reacting 1-(thiophen-2-yl)ethanone compound of formula-2

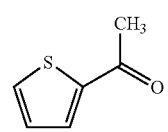

Formula-2 with dimethylamine hydrochloride compound of formula-3 in presence of paraformaldehyde in a suitable solvent selected from alcohols, preferably isopropyl alcohol gives the compound of formula-4,

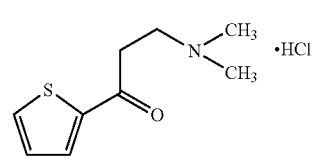

Formula-4 b) Purifying the compound of formula-4 to eliminate corresponding derivative of "DU-I" impurity, in a suitable solvent selected from alcohols like methanol, ethanol, isopropyl alcohol, with or without combination of water and/or ketones like acetone, methylisobutyl ketone with or without combination of water and/or mixtures thereof, preferably mixture of isopropyl alcohol and water to get the high pure compound of formula-4, c) Reducing the compound of formula-4 with an alkali metal borohydrides like sodium borohydride, potassium borohydride preferably sodium borohydride in a suitable solvent selected from $C_1$-$C_4$ alcoholic solvents, preferably methanol and isolating the compound of formula-5 in a suitable solvents like non-polar solvent and/or aliphatic hydrocarbon solvents and/or aromatic hydrocarbon solvents such as cyclohexane, toluene, hexanes and heptanes preferably cyclohexane and/or mixtures thereof,

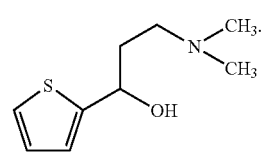

Formula-5 d) Resolving the compound of formula-5 with chiral acid like mandelic acid, tartaric acid, di-p-tolyl tartaric acid, dibenzoyl tartaric acid, camphor sulfonic acid, preferably L (+) mandelic acid in a suitable solvent selected from ester solvents like ethyl acetate, propylacetate, preferably ethyl acetate followed by purifying the corresponding salt in a suitable ester solvents selected from methyl acetate, ethyl acetate and isopropyl acetate preferably ethyl acetate to eliminate the corresponding derivative of R-isomer, further treating the obtained compound with weak inorganic base like sodium carbonate, sodium bicarbonate in suitable chloro solvents or ester solvents, preferably chloro solvents more preferably methylene chloride gives the compound of formula-6,

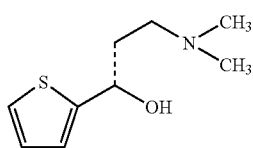

Formula-6 e) Reacting the compound of formula-6 with the compound of formula-7

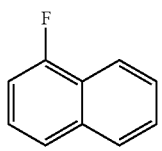

Formula-7 in presence of an alkali base like sodium hydroxide, potassium hydroxide preferably sodium hydroxide and in a suitable polar aprotic solvent like dimethylsulfoxide, dimethylformamide, which in situ demethylation followed by treating with oxalic acid gives Duloxetine oxalate salt compound of formula-8,

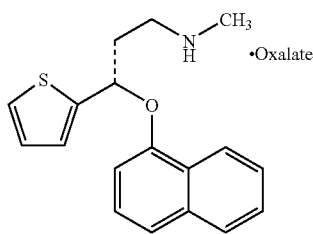

Formula-8 f) Converting the Duloxetine oxalate salt compound of formula-8 into its hydrochloride salt compound of formula-1 by adjusting the pH of the reaction mixture to 2 to 4 using suitable hydrochloric acid selected from ethyl acetate HCl, methanolic HCl, isopropyl alcohol HCl, preferably ethylacetate HCl in a suitable solvent like alcoholic solvents or ester solvents, preferably ester solvents more preferably ethyl acetate, g) Purifying the above obtained compound of formula-1 using suitable solvent or mixture of solvents selected from ester solvents like ethyl acetate, propyl acetate, methyl acetate, isopropyl acetate, methyl isopropyl acetate and/or alcohol solvents like methanol, ethanol, isopropyl alcohol and/or mixture of ester and alcohol solvents like ethyl acetate and methanol, ethyl acetate and ethanol, ethyl acetate and isopropyl alcohol, preferably mixture of solvents, more preferably ethyl acetate and methanol.

Related substances by HPLC of Duloxetine hydrochloride is carried out using a liquid chromatograph is equipped with variable wavelength UV-Detector, symmetry C8, 250×4.6 mm, 5 μm or equivalent column, 1.0 ml/min flow rate at 215 nm, ambient temperature, and the buffer is used 1.38 grams of sodium dihydrogen phosphate monohydrate in 300 ml water, dilute with water to 1000 ml, add 1.0 ml of TEA and pH is adjusted to 2.5 with phosphoric acid. Mobile phase A (degassed phosphate buffer), Mobile phase B (Acetonitrile:water in the ratio of 90:10 V/V)

R-Isomer content in mandelate salt of (S)-3-(dimethylamino)-1-(thiophen-2-yl) propan-1-ol by Chiral HPLC is carried out using a liquid chromatograph is equipped with variable wavelength UV-Detector, Chiralcel OJ, 250×4.6 mm column, 0.5 ml flow rate at 230 nm and ambient temperature, mobile phase is a mixture of 95 volumes of n-Hexane, volumes of ethanol, and 0.2 volumes of diethyl amine.

The thermal analysis of Duloxetine hydrochloride was carried out on Waters DSC Q-10 model differential scanning calorimeter and the FT-IR spectrum of Duloxetine hydrochloride was recorded on Thermo model Nicolet-380 as KBr pellet.

R-Isomer content in duloxetine hydrochloride by Chiral HPLC is carried out using a liquid chromatograph is equipped with variable wavelength UV-Detector, Chiralcel OJ-H, 250× 4.6 mm column, 1.0 ml flow rate at 230 nm and 40° C. temperature, mobile phase is a mixture of 90 volumes of n-Hexane, 10 volumes of ethanol, and 0.1 volumes of diethyl amine.

The present invention schematically represented as follows

Scheme-2:

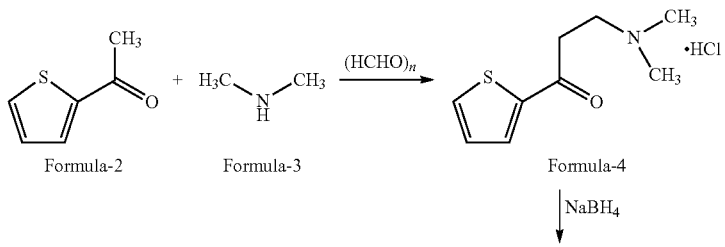

-continued
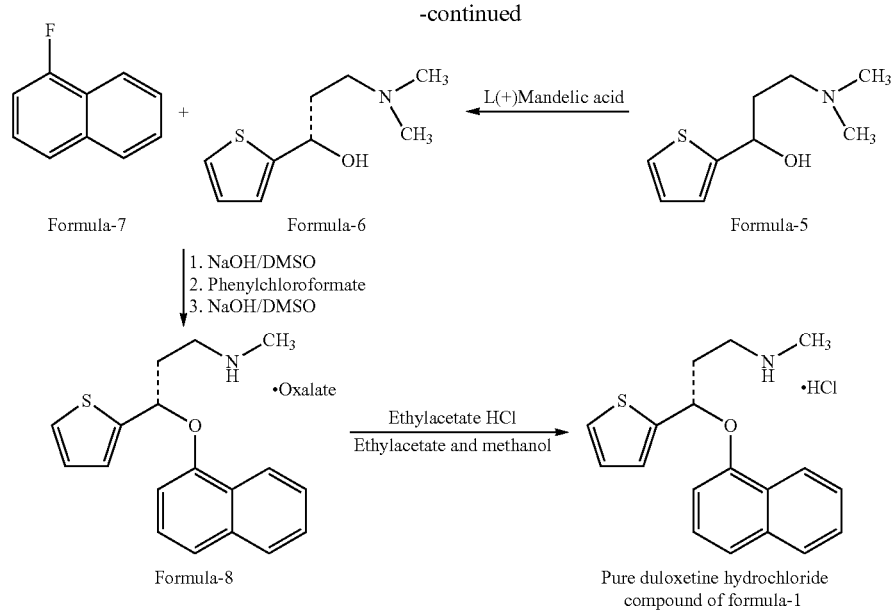
Scheme-3
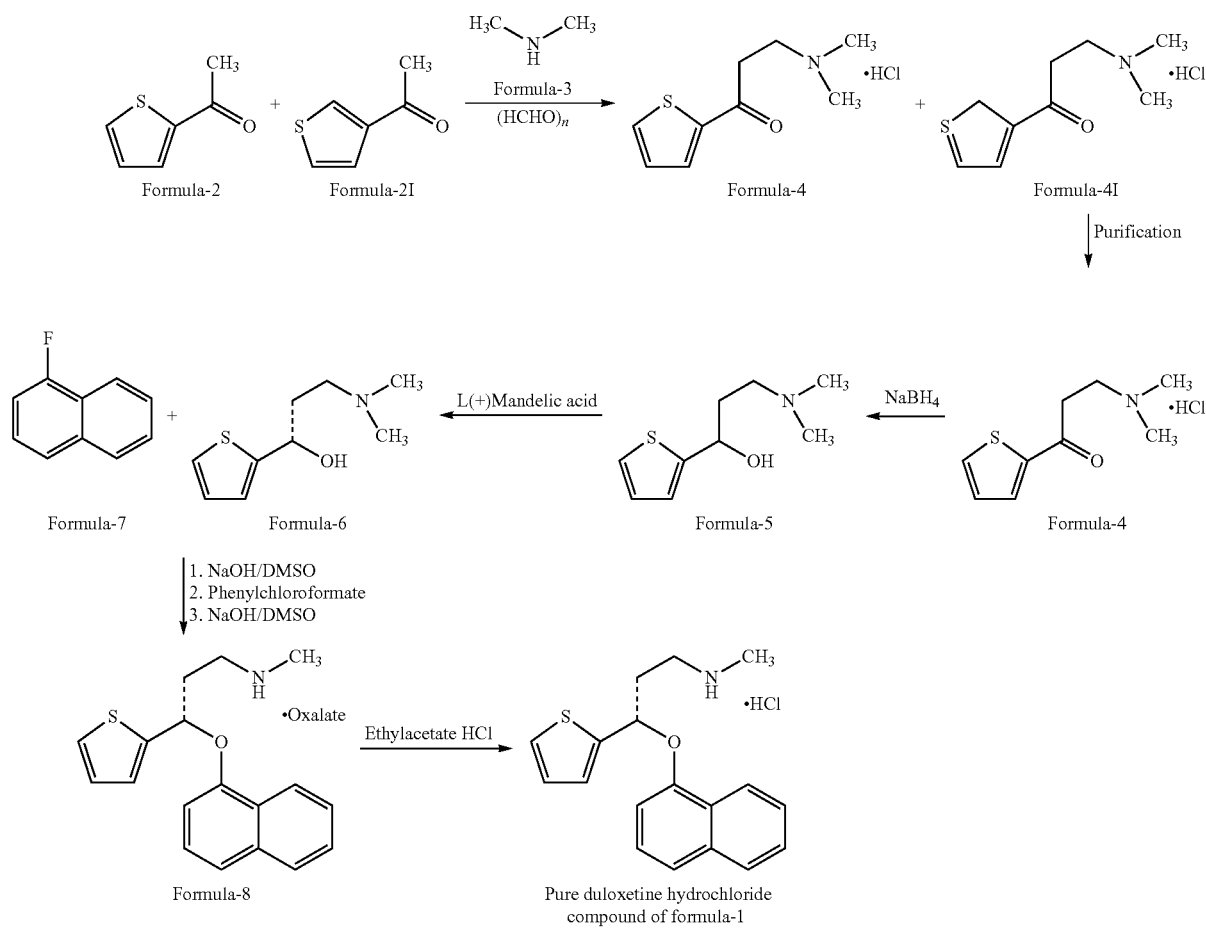

The present invention was demonstrated in examples illustrated below. These examples are provided as illustration only and therefore should not be construed as limitation of the scope of the invention.

EXAMPLES

Example-1

Preparation of 3-(dimethylamino)-1-(thiophen-2-yl) propan-1-one hydrochloride

Added 3.8 Kgs. of hydrochloric acid to a solution of 100 Kgs. of 2-acetyl thiophene, 81.5 Kgs. of dimethylamine hydrochloride, 35.4 Kgs. parafomaldehyde and 250 liters of isopropyl alcohol. Heated the reaction mixture to 75-80° C. Stirred the reaction mixture for 6 hours at 75-80° C. Cooled the reaction mixture to 0-5C. Stirred the reaction mixture for 2 hours at 0-5° C. Filtered the solid and washed with isopropyl alcohol.
Yield: 151 Kgs
M.R: 174-176° C.

Example-2

Purification of 3-(dimethylamino)-1-(thiophen-2-yl) propan-1-one hydrochloride

Added 1500 liters of isopropyl alcohol and 45 liters of water to 151 Kgs of 3-(dimethylamino)-1-(thiophen-2-yl) propan-1-one hydrochloride. Stirred the reaction mixture for 15 minutes at 25-30° C. Heated the reaction mixture to reflux. Stirred the reaction mixture for 2 hours at reflux. Cooled the reaction mixture slowly to 25-30° C. Stirred the reaction mixture for 4 hours at 25-30° C. Filtered the solid and washed with isopropyl alcohol. Dried the material at 25-30° C. for 2 hours followed by drying at 50-55° C. for 6 hours to get the pure title compound.
Yield: 144 Kgs.
M.R: 185-190° C.

Example-3

Purification of 3-(dimethylamino)-1-(thiophen-2-yl) propan-1-one hydrochloride

Added 1500 liters of acetone and 45 liters of water to 151 Kgs of 3-(dimethylamino)-1-(thiophen-2-yl) propan-1-one hydrochloride. Stirred the reaction mixture for 15 minutes at 25-30° C. Heated the reaction mixture to reflux. Stirred the reaction mixture for 2 hours at reflux. Cooled the reaction mixture slowly to 25-30° C. Stirred the reaction mixture for 4 hours at 25-30° C. Filtered the solid and washed with acetone. Dried the material at 25-30° C. for 2 hours followed by drying at 50-55° C. for 6 hours to get the pure title compound.
Yield: 142 Kgs.
M.R: 185-190° C.

Example-4

Preparation of 3-(dimethylamino)-1-(thiophen-2-yl) propan-1-ol

Added 50 liters of 20% sodium hydroxide solution to a cooled solution of 100 Kgs. of 3-(dimethylamino)-1-(thiophen-2-yl) propan-1-one hydrochloride, 100 liters of methanol and 25 liters of water at 0-5° C. Added a solution of 10 Kgs. of sodium borohydride in 50 liters of 20% sodium hydroxide to the above reaction mixture slowly at 0-5° C. in 5 hours. Allowed the reaction mixture temperature to 25-30° C. Stirred the reaction mixture for 6 hours at 25-30° C. Extracted the reaction mixture with methylene chloride. Separated the organic and aqueous layers. Extracted the aqueous layer with methylene chloride. Washed the organic layer with 10% sodium chloride solution. Distilled the solvent completely under reduced pressure at below 40° C. Added 25 liters of hexanes to the above reaction mixture. Distilled the solvent completely under reduced pressure at below 40° C. Added 100 liters of hexanes to the above reaction mixture. Heated the reaction mixture to reflux. Stirred the reaction mixture for 60 minutes. Cooled the reaction mixture to 0-5° C. and stirred the reaction mixture for 3 hours. Filtered the precipitated solid and washed with chilled hexanes. Dried the material at 50-55° C. for 6 hours to get the title compound.
Yield: 75 Kgs.
MR: 70-80° C.

Example-5

Preparation of (S) 3-(dimethylamino)-1-(thiophen-2-yl) propan-1-ol

Added 35 Kgs. of L(+)-mandelic acid to a solution of 70 Kgs. of 3-(dimethylamino)-1-(thiophen-2-yl) propan-1-ol and 700 liters of ethyl acetate at 25-30° C. Stirred the reaction mixture for 90 minutes at 25-35° C. Heated the reaction mixture to 70-75° C. Stirred the reaction mixture for 3 hours at 70-75° C. Cooled the reaction mixture to 25-35° C. Stirred the reaction mixture for 10 hours at 25-35° C. Filtered the precipitated mandelate salt of (S)-3-(dimethylamino)-1-(thiophen-2-yl) propan-1-ol compound and washed with ethyl acetate. Added 350 liters of ethyl acetate to the obtained mandelate salt of (S)-3-(dimethylamino)-1-(thiophen-2-yl) propan-1-ol compound. Heated the reaction mixture to 60-65° C. Stirred the reaction mixture for 60 minutes. Cooled the reaction mixture to 25-35° C. Stirred the reaction mixture for 90 minutes. Filtered the compound and washed with ethyl acetate. Dried the mandelate salt compound at 60-65° C. for 5 hours to get the pure mandelate salt of (S)-3-(dimethylamino)-1-(thiophen-2-yl) propan-1-ol compound free from corresponding derivative of R-isomer.
Yield: 62 Kgs.
Before Purification: MR: 113-115° C.; SOR: (+) 31° (C=1; Methanol) Corresponding derivative of R-isomer by Chiral HPLC: 7.0%
After Purification: MR: 121-124° C.; SOR: (+) 33° (C=1; Methanol) Corresponding derivative of R-isomer by Chiral HPLC: Nil A mixture of 62 Kgs. of mandelate salt of (S)-3-(dimethylamino)-1-(thiophen-2-yl) propan-1-ol, 125 liters of water and 375 liters of methylene chloride is cooled to 0-5° C. Adjusted the pH of the reaction mixture to 9.8 with 10% sodium carbonate solution at 0-5° C. Stirred the reaction mixture for 20 minutes at 0-5° C. Separated the organic and aqueous layers. Extracted the aqueous layer with methylene chloride. Washed the organic layer twice with 10% sodium chloride solution. Distilled the solvent completely under reduced pressure at below 35° C. Added 19 liters of cyclohexane to the above reaction mixture. Distilled the solvent completely under reduced pressure at below 35° C. Added 125 liters of cyclohexane to the above reaction mixture. Heated the reaction mixture to 40-45° C. and stirred for 60 minutes. Cooled the reaction mixture to 0-5° C. Filtered the precipitated solid and washed with cyclohexane. Dried the material at 40-45° C. for 6 hours to get the title compound.

Yield: 33 Kgs.

MR: 70-80° C.; SOR: (−) 6.20 (C=1; Methanol).

Example-7

Preparation of (S)-(+)-N-methyl-3-(1-naphthalenyloxy)-3-(2-thienyl) propanamine oxalate Heated a solution of 125 liters of dimethyl sulfoxide and 27 Kgs. of sodium hydroxide to 50-55° C. and Stirred for 45 minutes. Added a mixture of 25 Kgs. of (S)-3-(dimethylamino)-1-(thiophen-2-yl) propan-1-ol, 2.5 Kgs. of tertiary-butylammonium bromide and 30 Kgs. of 1-fluoronapthalene and 25 liters of dimethyl sulfoxide to the above reaction mixture at 50-55° C. Stirred the reaction mixture for 50 hours at 60-65° C. Cooled the reaction mixture to 15-20° C. Quenched the reaction mixture with water at 15-20° C. Extracted the reaction mixture with toluene. Separated the organic and aqueous layer. Washed the organic layer twice with water. Dried the organic layer with sodium sulphate. Added 27.5 Kgs. of diisopropylethylamine to the above reaction mixture at 25-35° C. Heated the reaction mixture to 43-48° C. Added 36 Kgs. of phenylchloroformate slowly to the reaction mixture at 43-45° C. Stirred the reaction mixture for 4 hours at 43-48° C. Cooled the reaction mixture to 20-25° C. Quenched the reaction mixture with water. Separated the organic and aqueous layers. Organic layer washed with acetic acid solution, oxalic acid followed by sodium bicarbonate solution. Distilled the solvent completely under reduced pressure at below 45° C. Added 500 liters of dimethylsulfoxide to the above obtained crude and heated to 40-45° C. Added sodium hydroxide solution (25 Kgs. in 100 liters of water) to the above reaction mixture at 40-45° C. for 3 hours. Further heated the reaction mixture to 50-55° C. Stirred the reaction mixture for 30 hours at 50-55° C. Cooled the reaction mixture to 15-20° C. and quenched the reaction mixture with water. Extracted the reaction mixture thrice with toluene and washed the organic layer twice with water. Added 17.5 Kgs. of Oxalic acid to the above organic layer at 25-30° C. Stirred the reaction mixture for 4 hours at 25-30° C. Filtered the precipitated solid and washed with toluene. Dried the material at 40-45° C. to get the title compound.

Yield: 36 Kgs.; M.R: 126-130° C.

Example-8

Preparation of (S)-(+)-N-methyl-3-(1-naphthalenyloxy)-3-(2-thienyl) propanamine hydrochloride A solution of 100 Kgs. of (S)-(+)-N-methyl-3-(1-naphthalenyloxy)-3-(2-thienyl) propanamine oxalate, 400 liters of water and 400 liters of methylene chloride is cooled to 0-5° C. Adjusted the pH of the reaction mixture 8.8 with aqueous ammonia. Stirred the reaction mixture for 15 minutes. Separated the organic layer and washed the organic phase with water. Distilled the solvent completely under reduced pressure at below 40° C. Added 400 liters of ethyl acetate to the above obtained crude. Cooled the reaction mixture to 0-5° C. Adjusted the pH of the reaction mixture to 2.0 with ethyl acetate HCl. Stirred the reaction mixture for 2 hours. Filtered the precipitated solid and washed with ethyl acetate. Dried the material at 45-50° C. to get the title compound.

Yield: 45 Kgs.

MR: 164-166° C.

Undesired R-isomer content by Chiral HPLC: 0.13%

HPLC Purity: 99.80%, 0.07% ("DU-I" impurity)

Example-9

Purification of Duloxetine Hydrochloride

Added 500 ml of ethyl acetate and 100 ml of methanol to 100 gr of Duloxetine hydrochloride. Heated the reaction mixture to 55-60° C. and stirred the reaction mixture at 55-60° C. for 90 minutes. Cooled the reaction mixture to 20-25° C. Stirred the reaction mixture for 4 hours at 20-25° C. Filtered the solid and washed with ethyl acetate. Dried the material at 55-60° C.

Yield: 70gr;

MR: 164-166° C.;

SOR: (+) 118° (C=1; Methanol);

Particle size: (d, 90): below 100 microns; Micronized material: (d, 90): below 25 microns;

Undesired R-isomer content by Chiral HPLC: 0.02%; HPLC Purity: 99.80% 0.02% ("DU-I" impurity).

What is claimed is:

1. A process for the preparation of a compound of Formula-1,

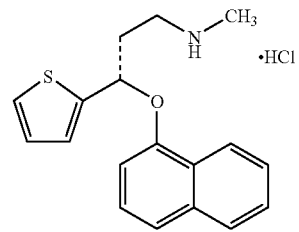

Formula-1 the process comprising:

a) reacting a compound of Formula-2

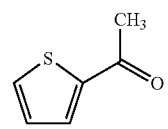

Formula-2 with dimethylamine hydrochloride in the presence of paraformaldehyde in an alcohol solvent to give a mixture of a compound of Formula-4 and a compound of Formula 4I,

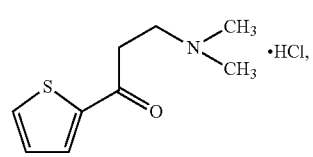

Formula-4

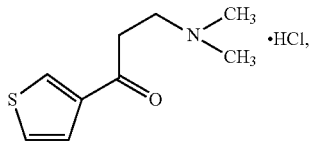

Formula-4I and separating the mixture of the compound of Formula-4 and the compound of Formula-4I from the alcohol solvent to obtain a separated mixture of the compound of Formula-4 and the compound of Formula-4I, b) heating the separated mixture in an alcohol solvent, with or without water, a ketone solvent, with or without water, or a mixture thereof, to reflux, cooling the separated mixture, and isolating the compound of Formula-4 from the separated mixture of the compound of Formula-4 and the compound of Formula-4I, c) reducing the compound of Formula-4 isolated in step b) with an alkali metal borohydride in a $C_1$-$C_4$ alcohol, and isolating a compound of Formula-5 in a non-polar solvent, or a mixture thereof,

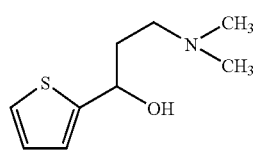

Formula-5 d) resolving the compound of Formula-5 with a chiral acid in an ester solvent, thereby forming a salt of the compound of Formula-5, then separating the R-isomer of the salt from the S-isomer of the salt in a second ester solvent, further treating the S-isomer of the salt with a weak inorganic base in a chlorinated or third ester solvent to yield a compound of Formula-6,

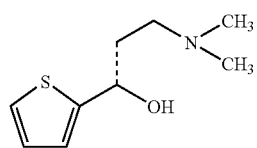

Formula-6 e) reacting the compound of Formula-6 with a compound of Formula-7,

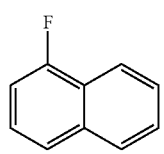

Formula-7 in the presence of an alkali base in a polar aprotic solvent to form a condensed compound, demethylating the condensed compound to form duloxetine and reacting duloxetine with oxalic acid to form a compound of Formula-8,

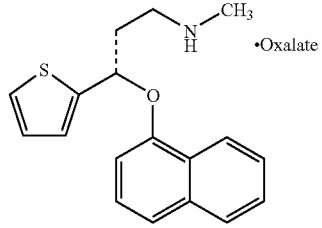

Formula-8 f) converting the compound of Formula-8 into the compound of Formula-1 by adjusting the pH of the reaction mixture to between 2 to 4 using a source of hydrochloric acid in an alcohol or ester solvent, and g) purifying the compound of Formula-1 using an ester solvent, an alcohol solvent, or a mixture thereof, to form the compound of Formula-1.

2. The process according to claim 1, wherein in step d) the chiral acid is L (+) mandelic acid.

3. The process according to claim 1, wherein in step d) the ester solvent, the second ester solvent and the third ester solvent are each ethyl acetate.

4. The process according to claim 1, wherein step e) is carried out without isolating the condensed compound or duloxetine.

5. The process according to claim 1, wherein in step f) the source of hydrochloric acid is ethyl acetate HCl.

6. The process according to claim 1, wherein the solvent in step b) is the alcohol solvent, with or without water, or the ketone solvent, with or without water.

7. The process according to claim 6, wherein the alcohol solvent is methanol, ethanol, or isopropyl alcohol.

8. The process according to claim 6, wherein the ketone solvent is acetone or methylisobutyl ketone.

9. The process according to claim 1, wherein the solvent in step b) is a mixture of isopropyl alcohol and water.

10. The process according to claim 1, wherein the solvent in step b) is a mixture of acetone and water.

11. The process according to claim 1, wherein the R-isomer of the salt is separated from the S-isomer of the salt in step d) by:
   a) slurrying the salt in the second ester solvent to form a mixture,
   b) heating the mixture to reflux,
   c) cooling the mixture to room temperature, and
   d) isolating the S-isomer of the salt by filtration.

12. The process according to claim 11, wherein the second ester solvent is ethyl acetate.

13. The process according to claim 1, wherein step g) comprises:
   i) dissolving the compound of Formula-1 in an ester solvent, an alcohol solvent, or a mixture-thereof, to form a mixture,
   ii) stirring the mixture,
   iii) cooling the mixture, and
   iv) isolating the compound of Formula-1 by filtration.

14. The process according to claim 13, wherein the solvent in step i) of step g) is a mixture of ethyl acetate and methanol.

15. The process according to claim 1, wherein
   in step a) the alcohol solvent is isopropyl alcohol;
   in step b) the alcohol solvent is methanol, ethanol or isopropyl alcohol, and the ketone solvent is acetone or methylisobutyl ketone;
   in step c) the alkali metal borohydride is sodium borohydride or potassium borohydride, the $C_1$-$C_4$ alcohol is methanol and the non-polar solvent for isolating the compound of formula-5 is cyclohexane, toluene, hexanes or heptanes;

in step d) the chiral acid is mandelic acid, tartaric acid, di-p-tolyl tartaric acid, dibenzoyl tartaric acid or camphor sulfonic acid, the ester solvent is ethyl acetate or propyl acetate, the second ester solvent is methyl acetate, ethyl acetate or isopropyl acetate, the weak inorganic base is sodium carbonate or sodium bicarbonate, and the S-isomer of the salt is treated with the weak inorganic base in a chlorinated solvent;

in step e) the alkali base is sodium hydroxide or potassium hydroxide, and the polar aprotic solvent is dimethylsulfoxide or dimethylformamide;

in step f) the source of hydrochloric acid is ethyl acetate HCl, methanolic HCl or isopropyl alcohol HCl in an ester solvent; or in step g) the ester solvent is ethyl acetate, propyl acetate, methyl acetate, isopropyl acetate or methyl isopropyl acetate, and the alcohol solvent is methanol, ethanol or isopropyl alcohol.

16. The process according to claim 1, wherein in step b) the solvent is a mixture of isopropyl alcohol and water;

in step c) the alkali metal borohydride is sodium borohydride and the non-polar solvent is cyclohexane;

in step d) the chiral acid is L (+) mandelic acid and the ester solvent is ethyl acetate, the second ester solvent is ethyl acetate, and the chlorinated solvent is methylene chloride;

in step e) the alkali base is sodium hydroxide;

in step f) the source of hydrochloric acid is ethyl acetate HCl, and the solvent is ethyl acetate; or in step g) the solvent is mixture of ethyl acetate and methanol.

* * * * *